US006428664B1

(12) United States Patent
Bhullar et al.

(10) Patent No.: US 6,428,664 B1
(45) Date of Patent: Aug. 6, 2002

(54) BIOSENSOR

(75) Inventors: Raghbir Singh Bhullar; Douglas Paul Walling, both of Indianapolis, IN (US)

(73) Assignee: Roche Diagnostics Corporation, Indianapolis, IN (US)

( * ) Notice: Subject to any disclaimer, the term of this patent is extended or adjusted under 35 U.S.C. 154(b) by 70 days.

(21) Appl. No.: 09/596,846

(22) Filed: Jun. 19, 2000

(51) Int. Cl.[7] ................................................ C12M 1/00
(52) U.S. Cl. ................................. 204/403.03; 204/409
(58) Field of Search ............................ 204/403, 409, 204/416, 418, 419, 403.03

(56) References Cited

U.S. PATENT DOCUMENTS

| | | | |
|---|---|---|---|
| 4,302,313 A | 11/1981 | Columbus | 204/195 R |
| 4,963,814 A | 10/1990 | Parks et al. | 323/274 |
| 4,999,582 A | 3/1991 | Parks et al. | 324/438 |
| 4,999,632 A | 3/1991 | Parks | 341/167 |
| 5,243,516 A | 9/1993 | White | 364/413.07 |
| 5,352,351 A | 10/1994 | White et al. | 204/406 |
| 5,366,609 A | 11/1994 | White et al. | 204/403 |
| 5,405,511 A | 4/1995 | White et al. | 204/153.1 |
| 5,407,554 A * | 4/1995 | Saurer | 204/403 |
| 5,413,690 A | 5/1995 | Kost et al. | 204/403 |
| 5,437,999 A | 8/1995 | Diebold et al. | 435/288 |
| 5,438,271 A | 8/1995 | White et al. | 324/444 |
| D369,216 S | 4/1996 | Micinski et al. | D24/169 |
| 5,575,403 A | 11/1996 | Charlton et al. | 221/31 |
| 5,630,986 A | 5/1997 | Charlton et al. | 422/64 |
| 5,762,770 A | 6/1998 | Pritchard et al. | 204/403 |
| 5,798,031 A | 8/1998 | Charlton et al. | 204/403 |
| 5,905,202 A | 5/1999 | Kubena et al. | 73/504.15 |
| 5,997,817 A | 12/1999 | Crismore et al. | 422/58 |
| 6,004,441 A | 12/1999 | Fujiwara et al. | 204/412 |
| 6,143,164 A * | 11/2000 | Heller et al. | 205/777.5 |

FOREIGN PATENT DOCUMENTS

| | | | |
|---|---|---|---|
| EP | 0 558 233 | 2/1993 | |
| EP | 0 763 730 | 3/1997 | |
| EP | 0 875 754 | 11/1998 | |
| EP | 0 934 771 A1 | 8/1999 | B01D/57/02 |
| EP | 0 964 059 | 12/1999 | |
| JP | 10002875 | 5/1998 | |
| WO | 98/49549 | 11/1998 | |

OTHER PUBLICATIONS

BASF product brochure for Terlux(TM) Methylmethacrylate/acrylnitrile/butadiene styrene polymer (MABS) Range Chart, Features, Applications and Typical Values (8pp).
Mitsubishi Kasei Corporation product brochure for Novarex(TM) Polycarbonate Resin (16pp).
Advanced Micro Systems, Inc., product brochure for SMC–C24/50 entitled, "High Performance Motor Controllers,"(2pp).
BASF product brochure for Terlux(TM) Methyl methacrylate/acrylate/acrylonitrile/butadiene/styrene polymer (MABS) Product Line, Properties and Processing (16pp.).

* cited by examiner

Primary Examiner—T. Tung
Assistant Examiner—Alex Noguerola
(74) Attorney, Agent, or Firm—Jill Woodburn

(57) ABSTRACT

A biosensor is provided in accordance with this invention. The biosensor includes a bottom section with an edge and a flange extending from the edge, a top section supported on the bottom section and having an edge and flange extending from the edge in alignment with the flange of the bottom section. The flanges of the top and bottom sections cooperate to form a capillary channel, and first and second electrodes. Additionally, the first electrode is positioned on the flange of the bottom section in the capillary channel and the second electrode is positioned on the flange of the top section in the capillary channel.

34 Claims, 15 Drawing Sheets

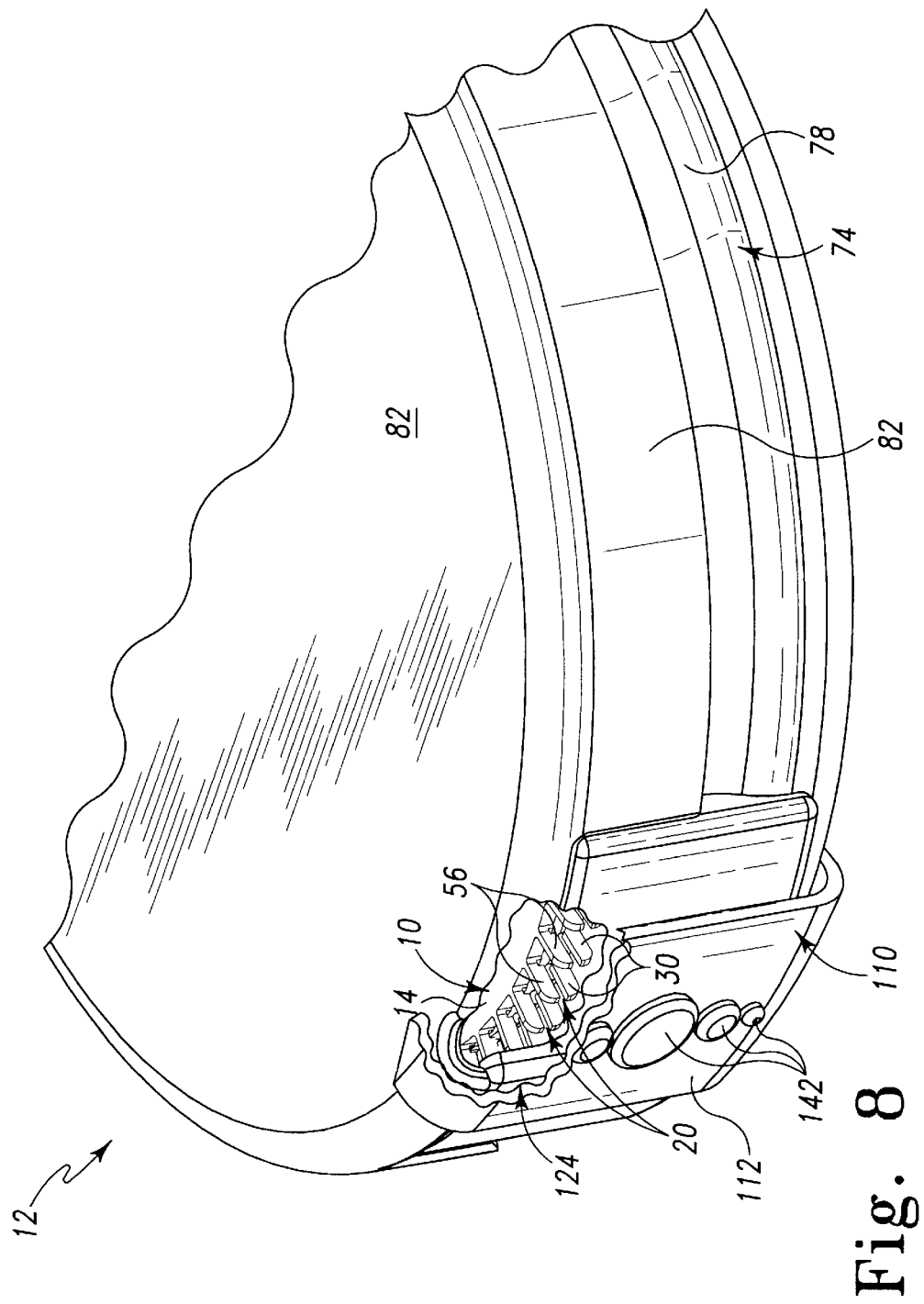

BIOSENSOR

FIELD OF THE INVENTION

The present invention relates to a biosensor and particularly to an electrochemical biosensor.

BACKGROUND AND SUMMARY OF THE INVENTION

Electrochemical biosensors are known. They have been used to determine the concentration of various analytes from biological samples, particularly from blood. Biosensors are described in U.S. Pat. Nos. 5,413,690; 5,762,770; 5,798, 031; and 5,997,817, the disclosure of each of which are hereby incorporated by reference.

According to the present invention a biosensor is provided. The biosensor comprises a bottom section with an edge and a flange extending from the edge, a top section supported on the bottom section and having an edge and flange extending from the edge in alignment with the flange of the bottom section, and first and second electrodes. The flanges of the top and bottom sections cooperate to form a capillary channel. Additionally, the first electrode is positioned on the flange of the bottom section in the capillary channel and the second electrode is positioned on the flange of the top section in the capillary channel.

A biosensor is also provided in accordance with the invention that comprises a first electrode including a base and a perimeter, a spacer situated on the base of the first electrode, and a second electrode including a base situated on the spacer and a perimeter. The perimeters of the first and second electrodes cooperate with one another to define a cantilevered capillary channel.

Still further, in accordance with the invention, a biosensor is provided that comprises a bottom section, a first electrode positioned on the bottom section, a spacer, and a second electrode. The first and second electrodes each include a base and a perimeter. The spacer is positioned adjacent to the bases of the first and second electrodes. Additionally, the perimeters of the first and second electrodes cooperate with one another to define a capillary channel.

Additional features of the invention will become apparent to those skilled in the art upon consideration of the following detailed description of the preferred embodiment exemplifying the best mode of carrying out the invention

BRIEF DESCRIPTION OF THE DRAWINGS

The detailed description particularly refers to the accompanying figures in which:

FIG. 8 is an enlarged perspective view of the biosensor and meter of FIG. 7 with portions of the meter broken away following closure of the lid and door of the meter;

DETAILED DESCRIPTION OF THE DRAWINGS

Figure 1:
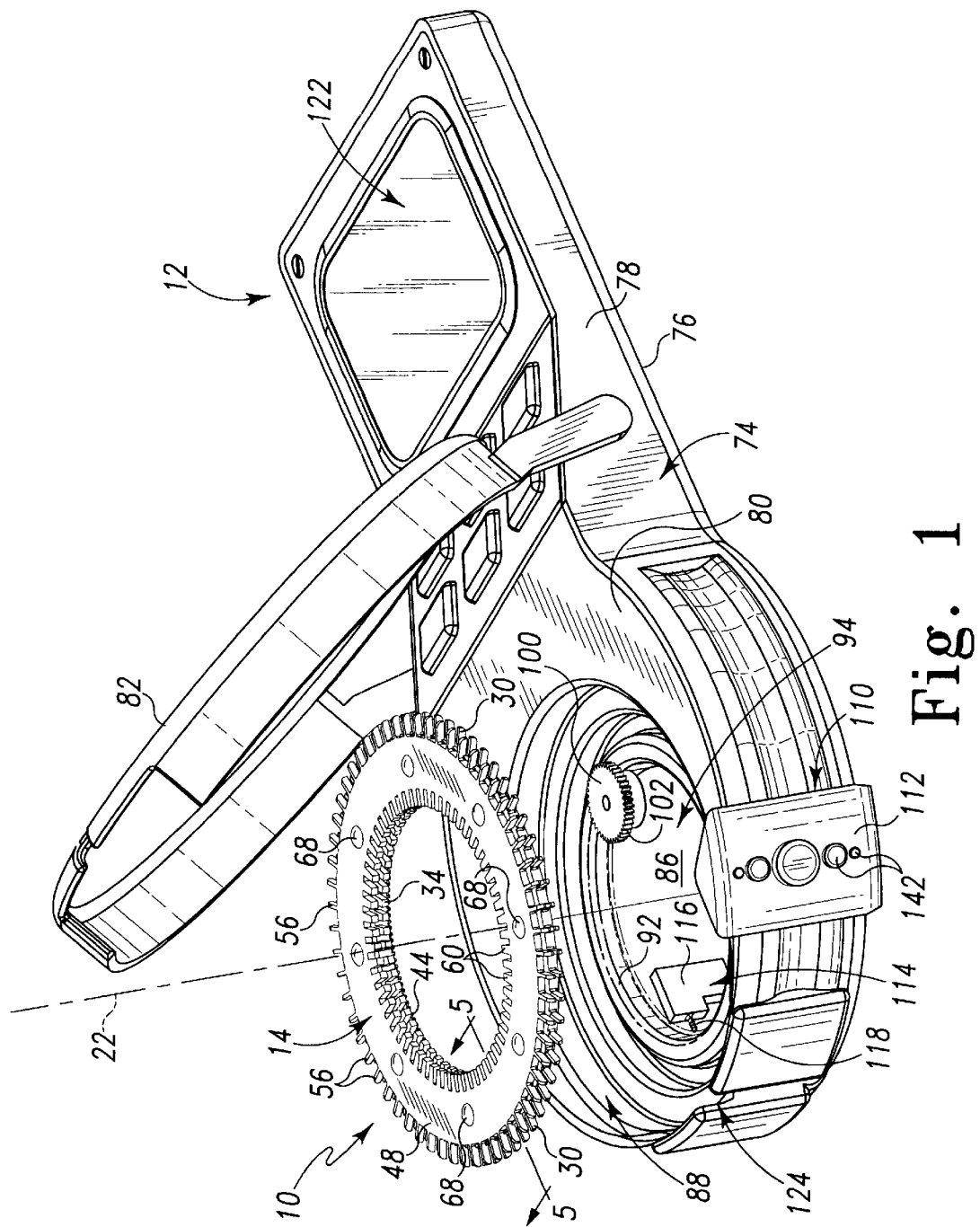
FIG. 1 is a perspective view of the biosensor, as it would appear to a user as it is being placed in a meter.
Figure 2:
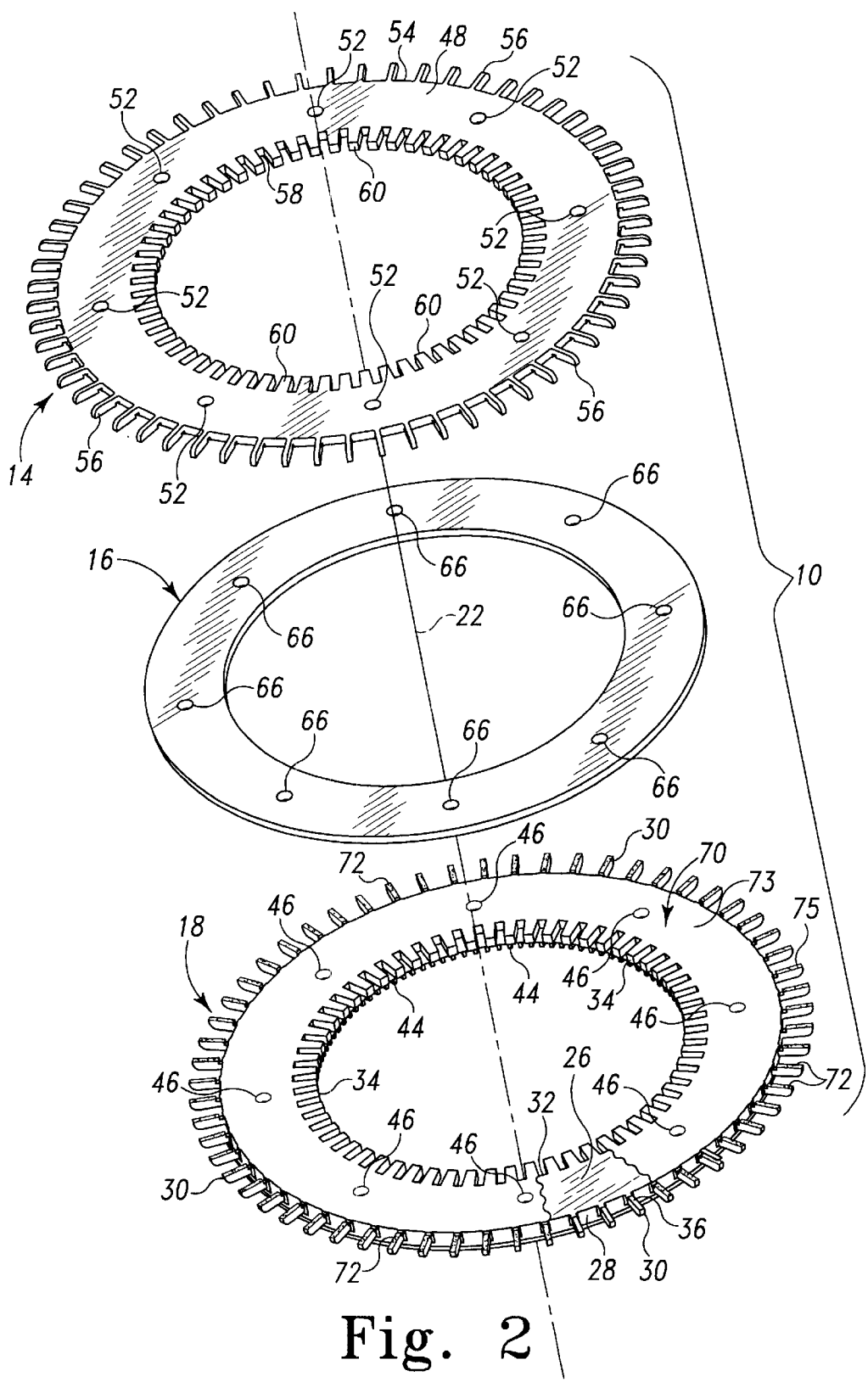
FIG. 2 is an exploded assembly view of the biosensor of FIG. 1, with portions of a bottom ring section broken away.

A biosensor 10 in accordance with the present invention is shown in FIG. 1, as it would appear to a user as it is being placed in a meter 12. Biosensor 10 compensates for small sample volumes by providing a cantilever based capillary design. As shown in FIG. 2, biosensor 10 includes a top ring section 14, a spacer 16, and a bottom ring section 18. Spacer 16 separates top and bottom sections 14, 1 8, which cooperate with one another to define a plurality of spaced-apart cantilevered capillary channels 20. Biosensor 10 is preferably disc-shaped and formed for rotation about an axis 22 in predetermined, discrete, increments to expose individual channels 20 to a user for testing. It is appreciated, however, that biosensor 10 can assume any number of shapes and can include as few as one cantilevered capillary channel 20 in accordance with this disclosure. Various aspects of the invention are presented in FIGS. 1–14, which are not drawn to scale and wherein like components in the several views are numbered alike.

Biosensor 10 of the present invention can be molded of a thermoplastic resin. Suitable resins include thermoplastics such as acrylonitrile butadine styrene (ABS), acetal, acrylic, polycarbonate (PC), polyester, polyethylene, fluroplastic, polimide, nylon, polyphenylene oxide, polypropylene (PP), styrene-acrylic copolymer, polystyrene, polysulphone, polyvinyl chloride, poly (methacrylate), poly (methyl methacrylate), or mixtures thereof. Preferably, top and bottom sections 14, 18 are formed from a polycarbonate, such as those used in making compact discs. More preferably, top and bottom sections 14, 18 do not contain any reinforcing material, and only contain a thermoplastic material such as polycarbonate. Specific examples of polycarbonates include MAKROLON 2400 from Bayer AG of Leverkusen, Germany, and NOVAREX® polycarbonate resin commercially available from Mitsubishi Kasei Corporation of Tokyo, Japan. Spacer 16 is preferably constructed of a heat-stabilized polyester film having a thickness of about 3 to about 7 mil. A non-limiting example of such a film is a clear polyester film, which is commercially available as MELTNEX ST-505 or ST 454, E.I. DuPont de Nemours and Company, Wilmington, Del. Spacer 16 has a height of about 75 to about 125 micrometers in thickness and is preferably has a height of about 75 micrometers. It is appreciated that height of spacer 16 may vary and that spacer 16 may include greater or fewer than eight apertures 66 in accordance with this disclosure.

Figure 3:
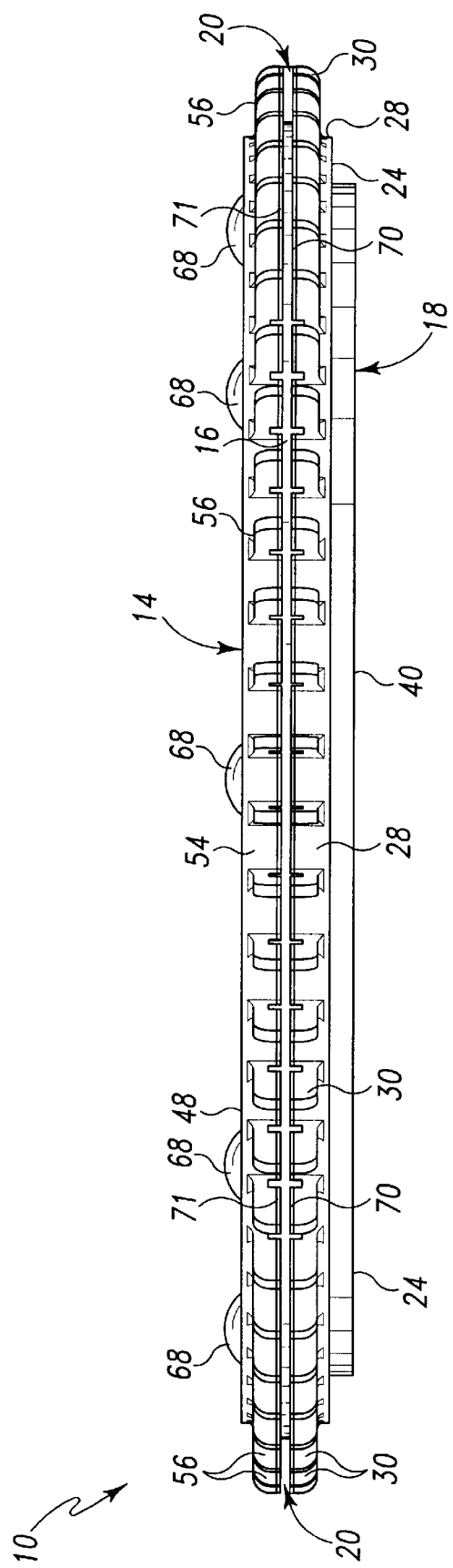
FIG. 3 is an assembled side view of the biosensor of FIG. 2.
Figure 4:
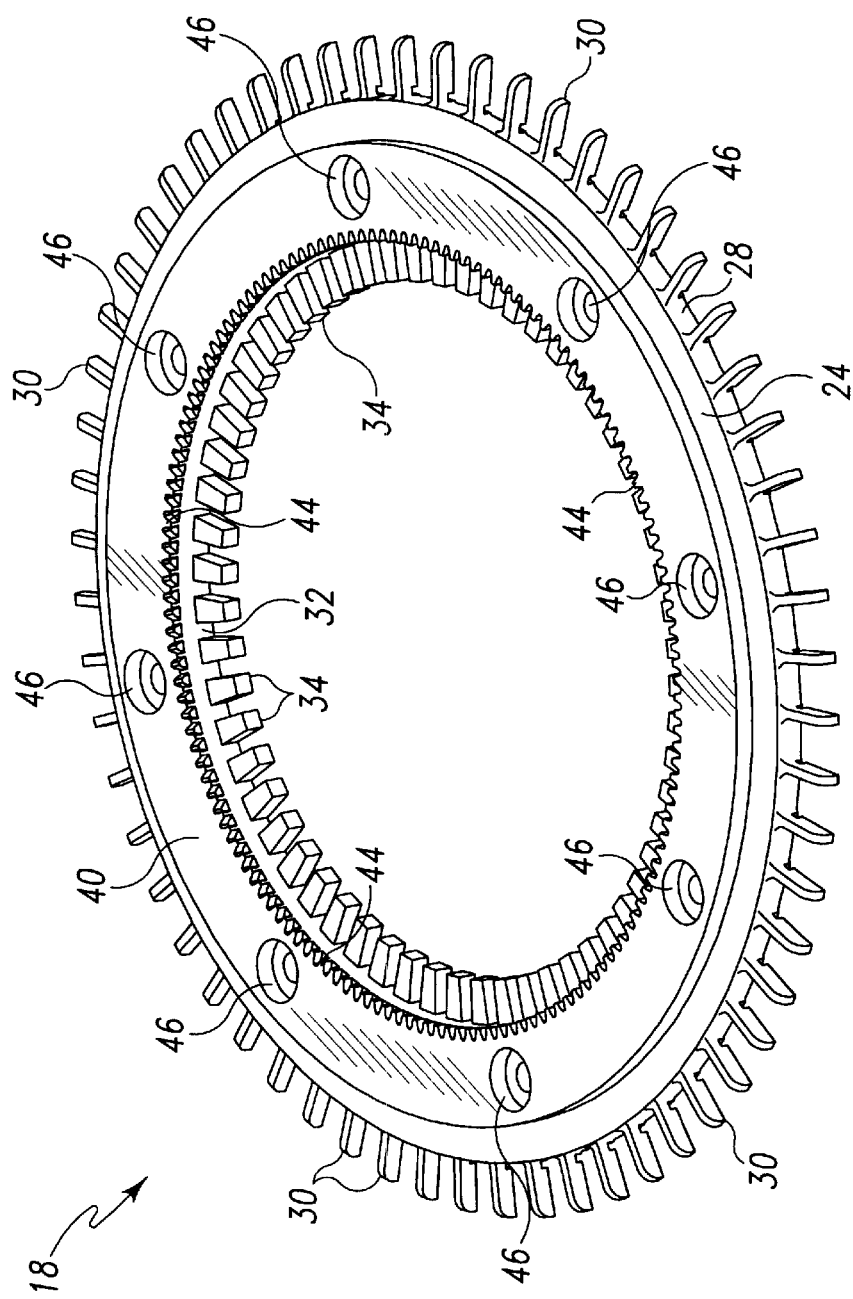
FIG. 4 is bottom perspective view of the bottom ring section of the biosensor of FIG. 2.
Figure 5:
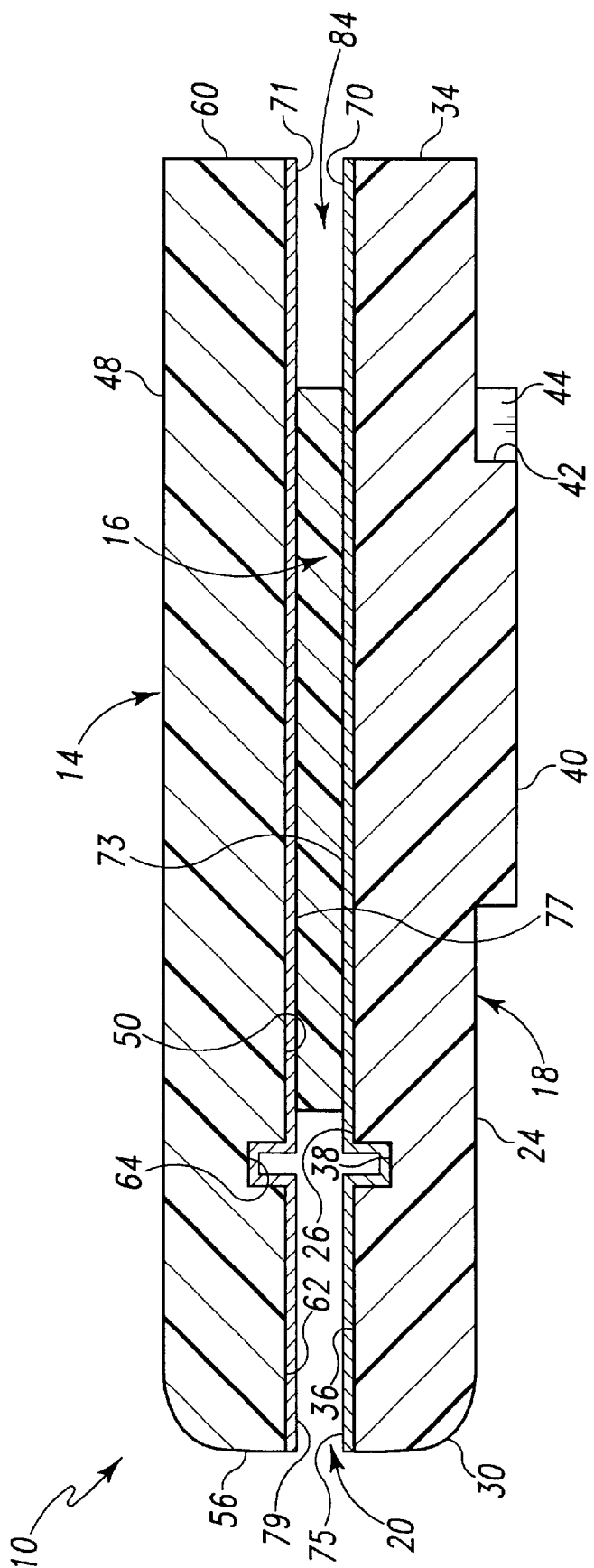
FIG. 5 is a view taken through lines 5—5 of FIG. 1.

As shown in FIGS. 2–5, bottom section 18 of biosensor 10 includes an outer side 24, an inner side 26 facing spacer 16, a circular outer edge 28 with a series of radially outwardly extending flanges 30, and a circular inner edge 32 with a series of radially inwardly extending flanges 34. Referring now to FIG. 5, a depression 38 extends between each flange 30 and inner side 26 of biosensor 10. In addition, each outer flange 30 includes an inner face 36 that is in general alignment with inner side 26.

As shown in FIGS. 4–5, outer side 24 of bottom section 18 includes an elevated portion 40 positioned adjacent to inner edge 32. Elevated portion 40 includes a circular inner edge 42 formed to include a series of radially inwardly extending teeth 44. Teeth 44 on outer side 24 are shaped and sized to mate in interlocking relation with meter 12 to rotate bottom section 18 of biosensor 10 about axis 22. In addition, bottom section 18 is formed to include eight apertures 46 extending between elevated portion 40 of outer side 24 and inner side 26. It is appreciated that bottom section 18 may include greater or fewer than eight apertures 46 in accordance with this disclosure.

Figure 6:
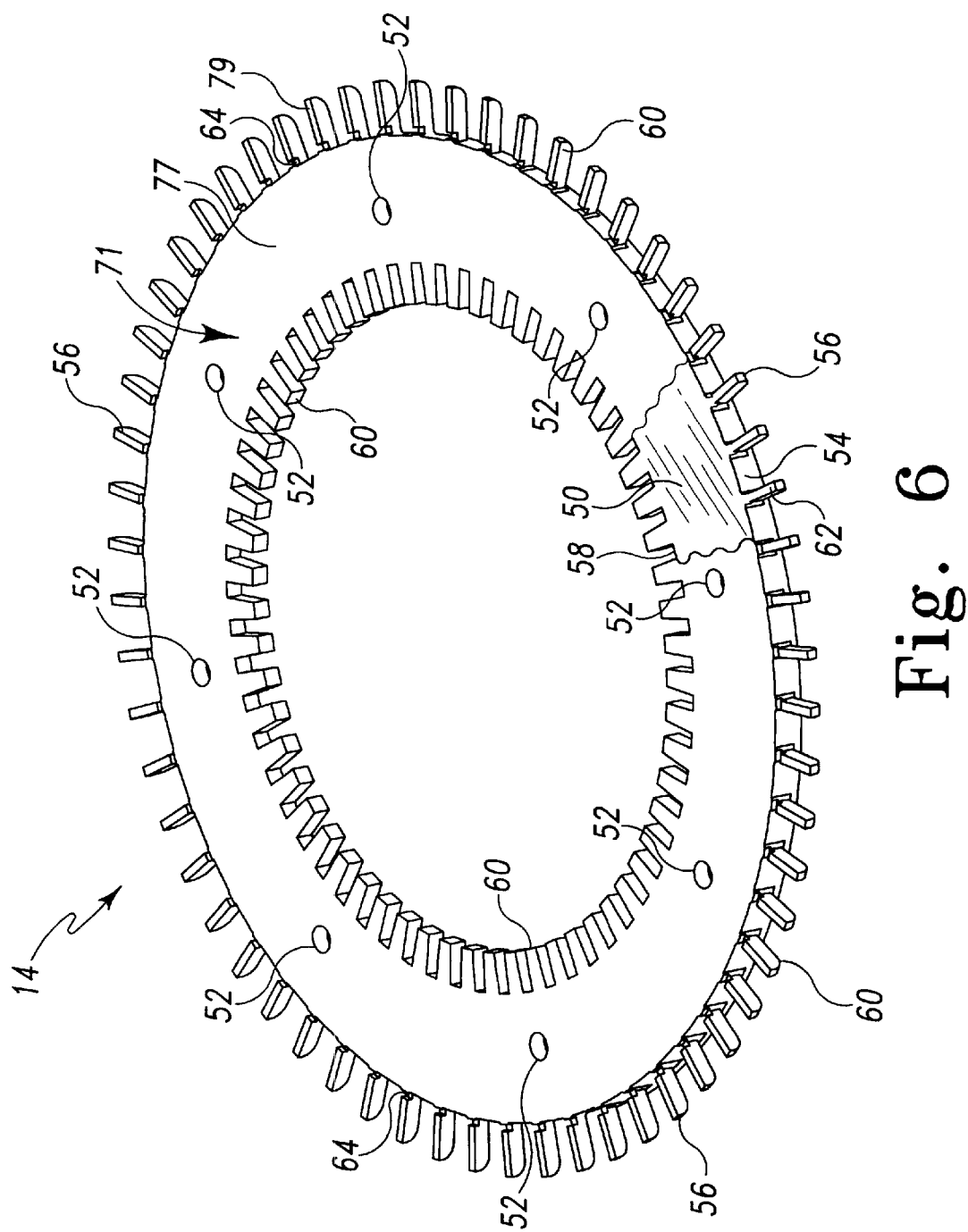
FIG. 6 is a bottom perspective view of the top ring section of the biosensor with portions broken away.
Figure 7:
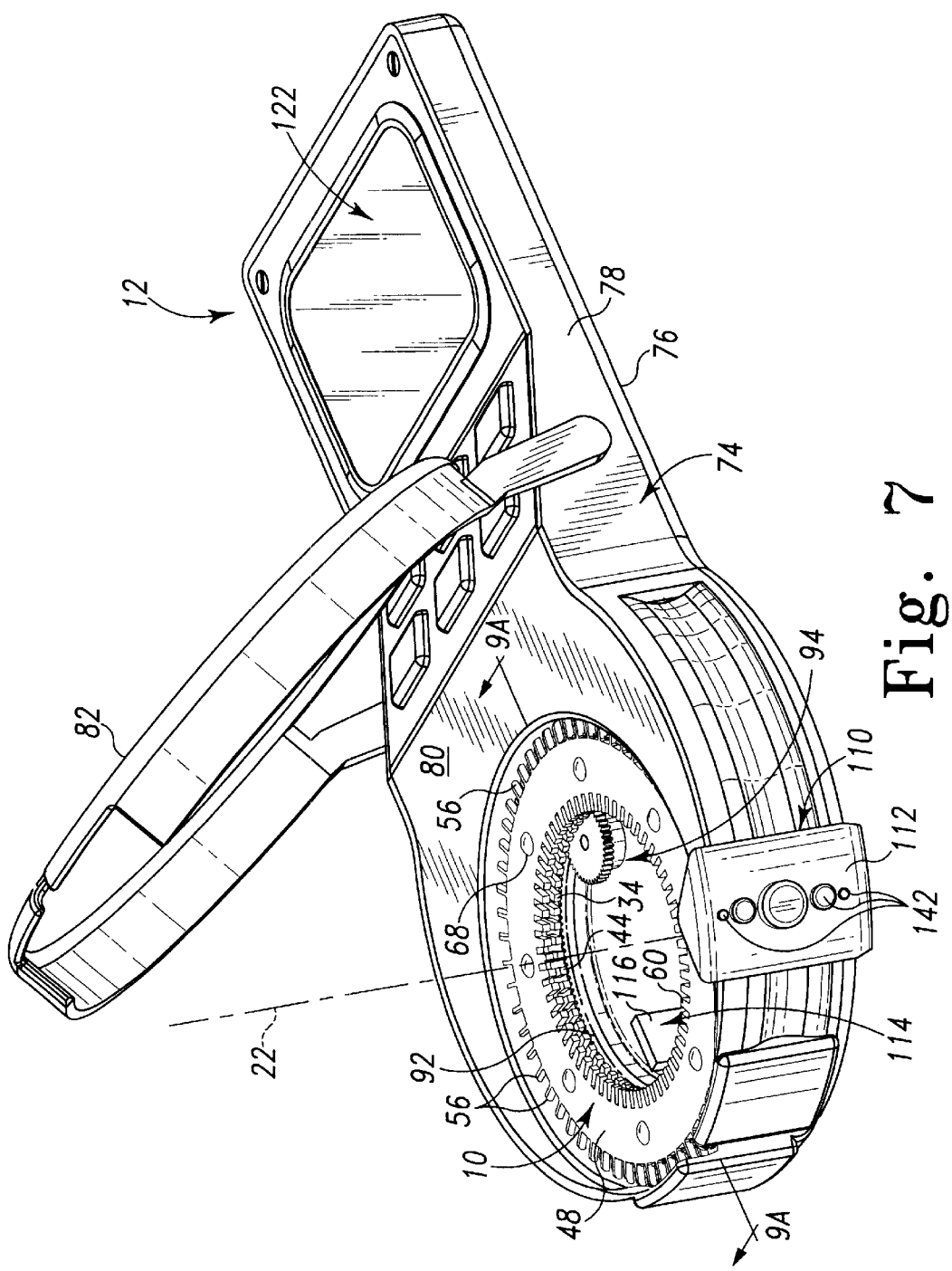
FIG. 7 is a perspective view of the biosensor of FIG. 1 positioned within the meter.

Now referring to FIGS. 2 and 3, top section 14 of biosensor 10 is supported on bottom section 18. As used herein with reference to the relative positioning of top and bottom sections 14, 18, the term "on" is used as a function word to indicate a position of top section 14 that is in close proximity with bottom section 18. It is appreciated that spacer 16 may be positioned between top and bottom sections 14, 18, or as discussed later, either top or bottom section 14, 18 may be formed integrally with the spacer. As shown in FIGS. 5–6, top section 14 has an outer side 48 and an inner side 50 facing spacer 16. Eight apertures 52 extend between outer and inner sides 48, 50 of top section 14 in general alignment with apertures 46 when biosensor 10 is assembled. It is appreciated that top section 14 may include greater or fewer than eight apertures in accordance with this disclosure. As shown in FIG. 6, top section 14 also includes a circular outer edge 54 with a series of radially outwardly extending flanges 56 and a circular inner edge 58 with a series of radially inwardly extending flanges 60. Each outer flange 56 includes an inner face 62 that is in general alignment with inner side 50 and a depression 64 that extends between inner face 62 and inner side 50. When biosensor 10 is assembled, inner face 62 of flange 56 faces inner face 36 of flange 30 to define capillary space 20.

Spacer 16 is positioned to lie between inner side 50 of top section 14 and inner side 26 of bottom section 18. Spacer 16 is formed to include eight apertures 66 that are aligned with apertures 46, 52 of bottom and top sections 18, 14 respectively. Spacer 16 positions inner sides 26, 50 of top and bottom sections 14, 18 apart a distance sufficient to prevent electrochemical events at inner side 26 from causing an electrochemical event at inner side 50.

Top and bottom sections 14, 18 are coupled to spacer 16 by connector pins 68. As shown in FIG. 1, biosensor 10 includes eight pins 68 that are each sized for extension through aligned apertures 52, 66, 46 respectively. Pins 68 are constructed from materials similar to top and bottom sections 14, 18. It is appreciated, however, that greater or fewer then eight pins 68 as well pins 68 having a variety of shapes and sizes may be used in accordance with this disclosure. It is also appreciated that top and bottom sections 14, 18 may be coupled to spacer 16 using staples, adhesives, ultrasonic bonding and the like in accordance with this disclosure.

Electrical conductors 71, 70 are laid down onto top and bottom sections 14, 18 respectively. Electrical conductors 71, 70 serve as the electrodes of biosensor 10. Therefore, conductor 70 may be a working electrode and conductor 71 may be a counter electrode. Referring now to FIG. 2, conductor 70 includes a base 73 extending across inner side 26 of bottom section 18 and a perimeter 75 at outer edge of flange 30 to place outer flange 30 and inner flange 34 in electrical communication with one another. Likewise, as shown in FIG. 6, conductor 71 includes a base 77 extending across inner side 50 and a perimeter 79 at outer edge of flange 56 to place outer flange 56 and inner flange 60 in electrical communication with one another. The distance between perimeters 75, 79 of conductors 71, 70 is about 35 to about 125 $\mu$m, more preferably 75 $\mu$m and defines capillary channel 20. It is appreciated that the distance between perimeters 75, 79 may vary.

Non-limiting examples of electrically-conductive materials suitable for forming electrical conductors 70, 71 include aluminum, carbon (such as graphite), cobalt, copper, gallium, gold, indium, iridium, iron, lead, magnesium, mercury (as an amalgam), nickel, niobium, osmium, palladium, platinum, rhenium, rhodium, selenium, silicon (such as highly doped polycrystalline silicon), silver, tantalum, tin, titanium, tungsten, uranium, vanadium, zinc, zirconium, mixtures thereof, and alloys or metallic compounds of these elements. Preferably, electrical conductors 70, 71 include gold, platinum, palladium, iridium, or alloys of these metals, since such noble metals and their alloys are unreactive in biological systems. Most preferably, conductor 70 is a working electrode made of gold, and conductor 71 is a counter electrode that is also made of gold and is substantially the same size as the working electrode.

Once biosensor 10 is assembled, as shown in FIGS. 3 and 5, spacer 16 positions top and bottom sections 14, 18 such that outer flanges 56, 30 cooperate with one another to define individual capillary channels 20. In a preferred embodiment, top and bottom sections 14, 18 each include sixty spaced-apart outer flanges 56, 30 respectively. It is appreciated, however, that top and bottom sections 14, 18 may each include as few as one or greater than sixty outer flanges in accordance with this disclosure. Moreover, the orientation of capillary channels 20 relative to one another is a design choice and may vary, non-limiting examples of which include a generally straight line, an S-shaped configuration, and an elliptical configuration in accordance with this disclosure.

Each capillary channel 20 exposes a portion of conductors 70, 71 between flanges 30, 56 for application of a sample to the exposed surfaces of conductors 70, 71. The degree to which conductors 70, 71 are exposed determines the surface area for each electrode. The working and counter electrodes each have substantially equivalent surface areas of less than or equal to about 2 mm$^2$, more preferably about 1.25 mm$^2$. It is appreciated, however, that the degree of exposure of conductors 70, 71 may vary in accordance with this disclosure.

As shown in FIG. 5, inner flanges 60, 34 cooperate with one another to define individual gaps 84. Each gap 84 exposes a portion of conductors 71, 70 between flanges 60, 34 for accessibility to meter 12 to conduct an electrochemical measurement. In a preferred embodiment, top and bottom sections 14, 18 each include sixty spaced-apart inner flanges 60, 34. It is appreciated that top and bottom sections 14, 18 may be formed without an inner flange or may be formed with any number of inner flanges in accordance with this disclosure so long as conductors 70, 71 are accessible to meter 12. Moreover, the orientation and height of gaps 84 relative to one another is a design choice and may vary. Non-limiting examples of orientation options include a generally straight line, an S-shaped configuration, and an elliptical configuration in accordance with this disclosure.

Reagent 72 provides electrochemical probes for specific analytes and may be positioned in each capillary channel 20.

Reagent 72 is placed as a film of generally uniform thickness over at least a portion of perimeter 75 of conductor 70 on each flange 30. See for example FIG. 2. The choice of specific reagent 72 depends on the specific analyte or analytes to be measured, and are well known to those of ordinary skill in the art. For example, a reagent for measuring glucose from a whole blood sample may be used as reagent 72 of the present invention. A non-limiting example of a reagent for measurement of glucose in a human blood sample contains 62.2 mg polyethylene oxide (mean molecular weight of 100–900 kilodaltons), 3.3 mg NATROSOL 250M, 41.5 mg AVICEL RC-591 F, 89.4 mg monobasic potassium phosphate, 157.9 mg dibasic potassium phosphate, 437.3 mg potassium ferricyanide, 46.0 mg sodium succinate, 148.0 mg trehalose, 2.6 mg TRITON X-100 surfactant, and 2,000 to 9,000 units of enzyme activity per gram of reagent. The enzyme is prepared as an enzyme solution from 12.5 mg coenzyme PQQ and 1.21 million units of the apoenzyme of quinoprotein glucose dehydrogenase. This reagent is further described in U.S. Pat. No. 5,997,817, the disclosure of which is incorporated herein by reference.

Another example of a suitable reagent is one for determining hematocrit. When, for example, hematocrit is to be determined, the reagent includes oxidized and reduced forms of a reversible electroactive compound (potassium hexacyanoferrate (III) ("ferricyanide") and potassium hexacyanoferrate (II) ("ferrocyanide"), respectively), an electrolyte (potassium phosphate buffer), and a microcrystalline material (Avicel RC-591F - a blend of 88% microcrystalline cellulose and 12% sodium carboxymethylcellulose, available from FMC Corp.). Concentrations of the components within the reagent before drying are as follows: 400 millimolar (mM) ferricyanide, 55 mM ferrocyanide, 400 mM potassium phosphate, and 2.0% (weight: volume) Avicel. A further description of the reagent for a hematocrit assay is found in U.S. Pat. No. 5,385,846, the disclosure of which is incorporated herein by reference. Other non-limiting examples of enzymes and mediators that may be used in measuring particular analytes in biosensor 10 of the present invention are listed below in Table 1.

TABLE 1

| Analyte | Enzymes | Mediator (Oxidized Form) | Additional Mediator |
|---|---|---|---|
| Glucose | Glucose Dehydrogenase and Diaphorase | Ferricyanide | |
| Glucose | Glucose-Dehydrogenase (Quinoprotein) | Ferricyanide | |
| Cholesterol | Cholesterol Esterase and Cholesterol Oxidase | Ferricyanide | 2,6-Dimethyl-1, 4-Benzoquinone 2,5-Dichloro-1, or Phenazine Ethosulfate |
| HDL Cholesterol | Cholesterol Esterase and Cholesterol Oxidase | Ferricyanide | 2,6-Dimethyl-1, 4-Benzoquinone 2,5-Dichloro-1, 4-Benzoquinone or Phenazine Ethosulfate |

TABLE 1-continued

| Analyte | Enzymes | Mediator (Oxidized Form) | Additional Mediator |
|---|---|---|---|
| Triglycerides | Lipoprotein Lipase, Glycerol Kinase, and Glycerol-3-Phosphate Oxidase | Ferricyanide or Phenazine Ethosulfate | Phenazine Methosulfate |
| Lactate | Lactate Oxidase | Ferricyanide | 2,6-Dichloro-1, 4-Benzoquinone |
| Lactate | Lactate Dehydrogenase and Diaphorase | Ferricyanide, Phenazine Ethosulfate, or Phenazine Methosulfate | |
| Lactate Dehydrogenase | Diaphorase | Ferricyanide | Phenazine Ethosulfate, or Phenazine Methosulfate |
| Pyruvate | Pyruvate Oxidase | Ferricyanide | |
| Alcohol | Alcohol Oxidase | Phenylenediamine | |
| Bilirubin | Bilirubin Oxidase | 1-Methoxy-Phenazine Methosulfate | |
| Uric Acid | Uricase | Ferricyanide | |

In some of the examples shown in Table 1, at least one additional enzyme is used as a reaction catalyst. Also, some of the examples shown in Table 1 may utilize an additional mediator, which facilitates electron transfer to the oxidized form of the mediator. The additional mediator may be provided to the reagent in lesser amount than the oxidized form of the mediator.

While the above reagents are described with reference to an amperometric assay, it is contemplated that current, charge, impedance, conductance, potential, or other electrochemically indicated property of sample might be accurately correlated to the concentration of the analyte in sample with biosensor 10 in accordance with this disclosure.

Referring again to FIG. 1, meter 12 is suitable for receiving biosensor 10. Meter 12 includes a shell 74 that has a base 76, a wall 78 extending from base 76, and a cover 80 that extends across wall 78 over a first portion of base 76. Meter 12 also includes a lid 82 coupled to wall 78 and formed for pivoting movement across a second portion of base 76 and a door 110. It is appreciated that the shape of shell 74 is a design choice and may vary, non-limiting examples of which include a rectangular, an elliptical, and a triangular configuration in accordance with this disclosure.

Figure 9A:
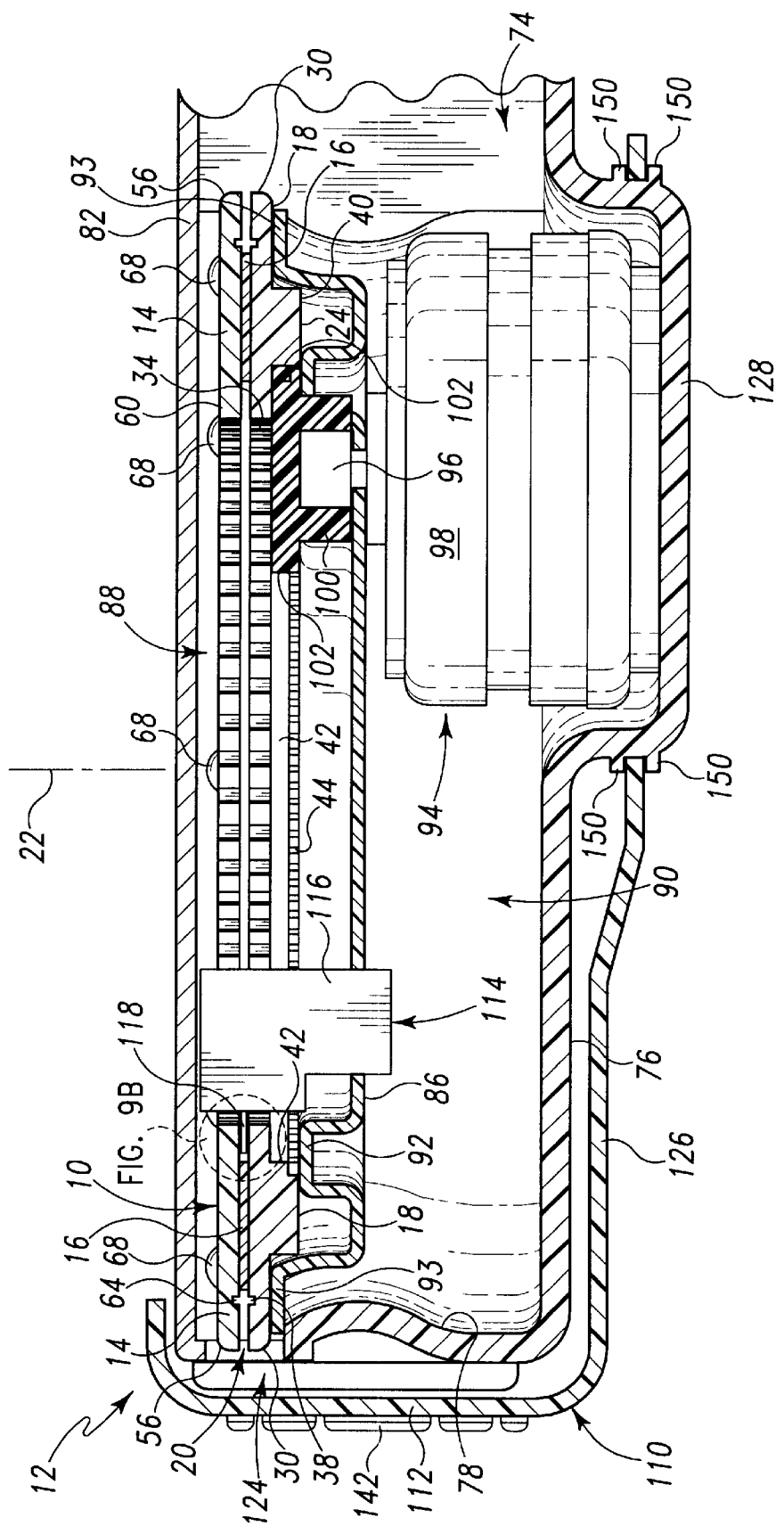
FIG. 9A is a view taken through lines 9A—9A of FIG. 7.
Figure 9B:
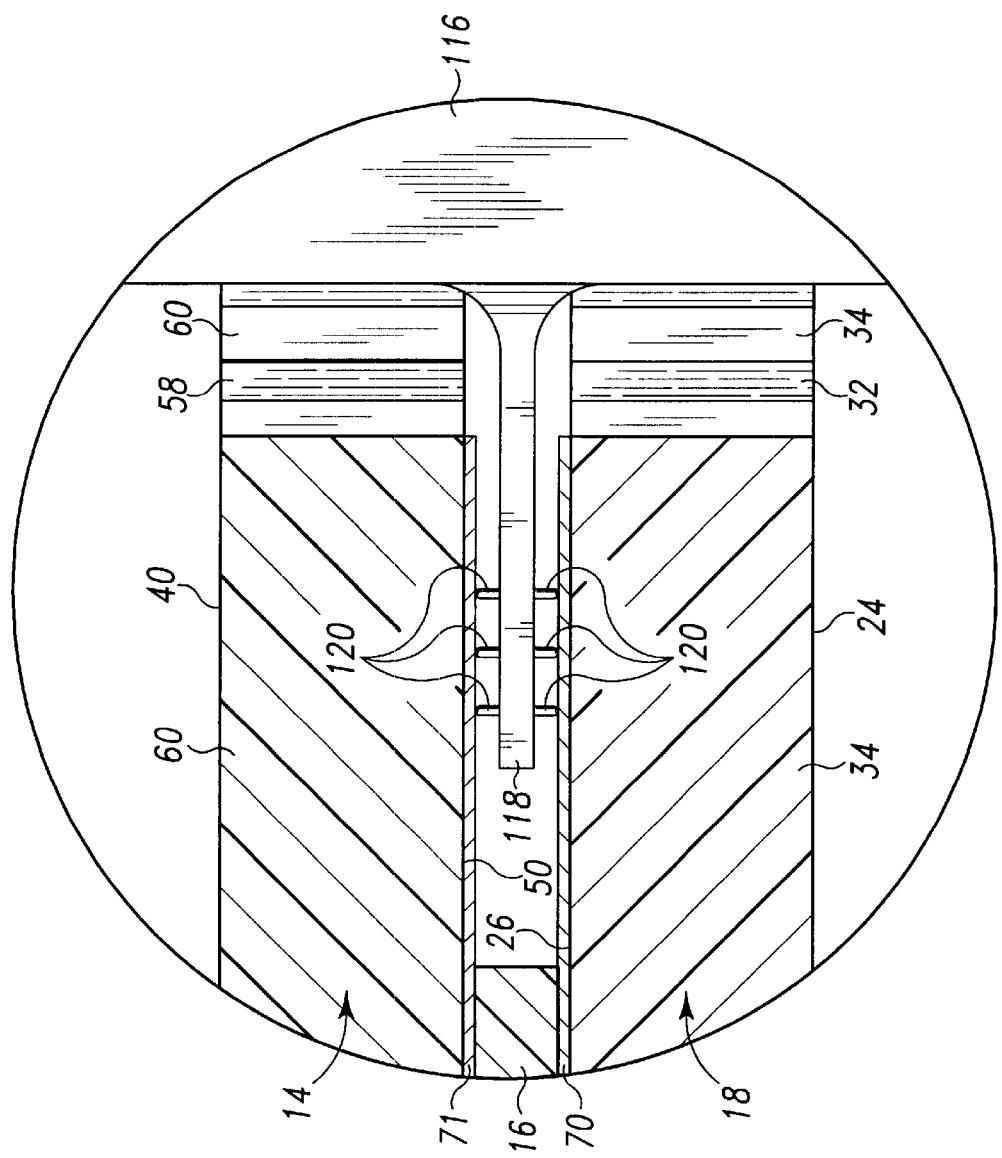
FIG. 9B is an enlarged view of the biosensor and meter shown in FIG. 9A.

Door 110 of shell 74 includes a screen 112 that covers an opening 124 in wall 78 when door 110 is in a closed position as shown in FIG. 8. Door 110, as shown in FIG. 9A, also includes a pivot arm 126 that extends between screen 112 and base 76. Screen 112 is formed to pivot away from opening 124 to an open position (FIGS. 1 and 7) and includes raised portions 142 that serve as finger grips to a user during this pivoting movement. Pivot arm 126 of door 110 is formed for rotation about a recessed portion 128 of base 76. Recessed portion 128 includes spaced-apart tabs 150 and pivot arm 126 is held between tabs 150 and rotates about recessed portion 128. It is appreciated that door 110 could pivot, detach, or fold relative to wall 78 or meter 12 could be formed without a door in accordance with this disclosure.

Shell 74 of meter 12 also includes a partition 86 defining upper and lower cavities 88, 90. Partition 86 includes support portions 92, 93 extending into upper cavity 88 for supporting outer side 24 of bottom section 18. In addition, a biosensor-drive system 94 is housed in lower cavity 90. Biosensor-drive system 94 is configured to apply a force to bottom section 18 to rotate biosensor 10 in upper cavity 88 of meter 12.

Figure 10:
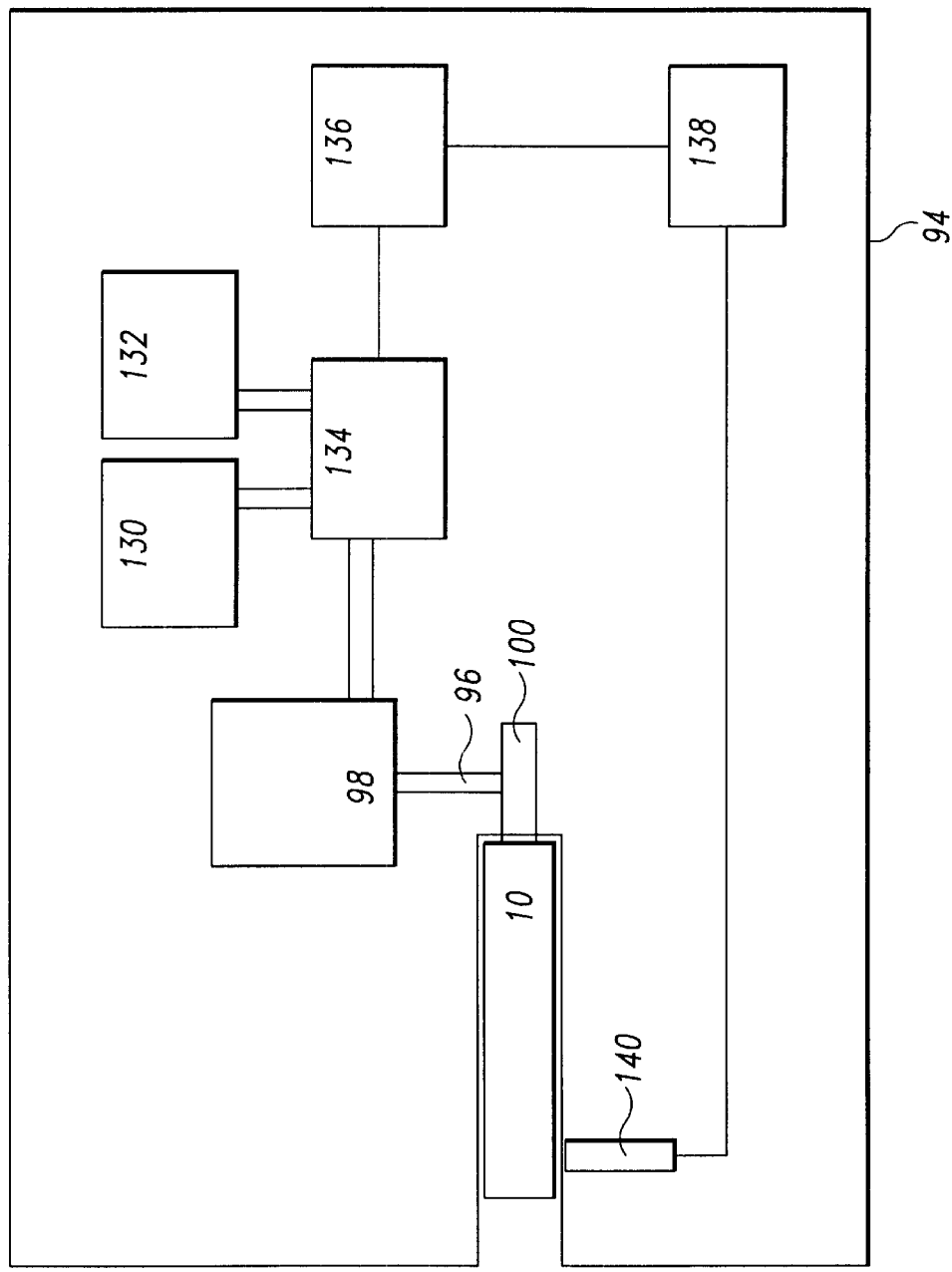
FIG. 10 is a diagrammatic view of a biosensor-drive system of the present invention.

As shown in FIGS. 9A and 10, biosensor-drive system 94 includes a motor shaft 96 turned by motor 98 and a drive wheel 100 fixed or keyed to motor shaft 96 to turn therewith. Drive wheel 100 includes teeth 102 that correspond with teeth 44 of bottom section 18. Therefore, rotational movement of motor shaft 96 and drive wheel 100 will in turn rotate biosensor 10 about axis 22. Biosensor-drive system 94 also includes an actuator system that has an electrical circuit containing a battery power supply 130, a clock 132, a motor drive integrated circuit 134, a meter CPU 136, a signal interface 138, and a proximity sensor 140. Integrated circuit 134 is preferably an SMC-C24/50 Intelligent Motion Control IC, which is commercially available from Advanced Micro Systems, Inc., Nashua, NH. Integrated circuit 134 is in communication with battery 130, clock 132, and motor 98. In addition, meter CPU 136 is in communication with circuit 134 and signal interface 138. Preferably, proximity sensor 140 is located adjacent to biosensor 10 and in communication with signal interface 138 and is formed to ensure that conductive members 120 engage electrodes 70, 71.

The angular impulse generated by motor 98 is generally in a consistent direction of travel so that the impulse does not rotate biosensor 10 in a direction that exposes a used testing site to the user. If, however, proximity sensor 140 detects that biosensor 10 has rotated a new testing site past opening, motor 98 will generate an angular impulse that will rotate biosensor 10 in an opposite direction of travel to position the new testing site in the desired location adjacent to opening 124. The run time of motor 98 is controlled by the rotational position of biosensor 10 about axis 22. Specifically, motor 98 will run and torque will be applied to biosensor 10 via drive wheel 100 and motor shaft 96 until proximity sensor 140 detects that conductive members 120 engage electrodes 70, 71. The start time of motor 98 is controlled by the user following completion of the test.

In use, the user presses a button on meter 12 that creates an electrical engagement of motor drive integrated circuit 134, which starts electric motor 98. Motor 98 is turned off once biosensor 10 has reached a pre-determined rotational position about axis 22 to expose a new testing site to the user. Moreover, integrated circuit is programmed to have a trip point, which is a programmable position that allows pre-defined operations to be triggered, such as alerting the user that the biosensor 10 is spent, when the position of motor 98 matches the established trip point position. During motion, the position counter of circuit 134 is continuously updated and compared to the programmed trip position. There are many ways to cause biosensor-drive system 96 operate in meter 12 as will be readily be understood by one of ordinary skill in the art without exceeding the scope of this disclosure.

Meter 12 includes a connector assembly 114 that has a post 116 extending away from partition 86 into upper cavity 88 and a tab 118 that extends from post 116 toward wall 78. Tab 118 includes six electrically conductive members 120, three of which extend from the top side and three of which extend from the bottom side of tab 118. Members 120 are each in electrical communication with meter CPU 136 housed in first portion of meter 12. Tab 118 is somewhat flexible so members 120 will engage inner flanges 34, 60 when biosensor 10 is coupled to meter 12. It is appreciated that the number and configuration of members 120 may vary in accordance with this disclosure.

Electronic components (not shown) of meter 12 are in communication with members 120. These components will normally be adapted to apply an algorithm to the current measurement, whereby an analyte concentration is provided and visually displayed on display 122. Improvements in components are the subject of commonly assigned U.S. Pat. No. 4,963,814, issued Oct. 16, 1990; U.S. Pat. No. 4,999,632, issued Mar. 12, 1991; U.S. Pat. No. 4,999,582, issued Mar. 12, 1991; U.S. Pat. No. 5,243,516, issued Sep. 7, 1993; U.S. Pat. No. 5,352,351, issued Oct. 4, 1994; U.S. Pat. No. 5,366,609, issued Nov. 22, 1994; White et al., U.S. Pat. No. 5,405,511, issued Apr. 11, 1995; and White et al., U.S. Pat. No. 5,438,271, issued Aug. 1, 1995, the disclosures of which are hereby incorporated by reference.

Many fluid samples may be analyzed. For example, human body fluids such as whole blood, plasma, sera, lymph, bile, urine, semen, cerebrospinal fluid, spinal fluid, lacrimal fluid and stool specimens as well as other biological fluids readily apparent to one skilled in the art may be measured. Fluid preparations of tissues can also be assayed, along with foods, fermentation products and environmental substances, which potentially contain environmental contaminants. Preferably, human serum is assayed with this invention.

To install biosensor 10 in meter 12, a user pivots door 110 away from opening 124, as shown in FIG. 1, and lifts lid 82 of meter 12 to expose upper cavity 88 and partition 86. The user then inserts biosensor 10 into upper cavity 88 until outer side 24 of bottom section 18 rests upon supports 92, 93, teeth 44 of bottom section 18 engage teeth 102 of drive wheel 100, and tab 118 extends into gap 84 so that members 120 engage flanges 34, 60. The user then closes lid 82. Proximity sensor 140 will detect the position of biosensor 10 and will relay that information to circuit 134 via signal interface 138 and meter CPU 136. If necessary, motor 98 is actuated to rotate biosensor 10 until a pre-determined rotational position is reached, exposing a new testing site to the user. The user may then conduct a test, or close door 110 over opening to seal biosensor 10 in upper cavity 88.

To conduct a test with biosensor 10, the user opens door 110, if necessary, to expose at least one capillary channel 20. A liquid sample (not shown) is deposited between outer flanges 30, 56 into capillary channel 20. Capillary action draws the sample containing the analyte through channel 20 to dissolve reagent 72. Sample will travel through channel 20 until it encounters depressions 38, 64, where due to the increased dimensions of channel, capillary action is drastically decreased. When reagent 72 is formed in accordance with the non-limiting example as described above for purposes of measurement of glucose in a human blood sample using an amperometric measurement, the analyte is oxidized and the oxidized form of the mediator is reduced once reagent 72 is dissolved in sample. The reaction between the analyte and reagent 72 is permitted to go to completion. (Completion is defined as sufficient reaction involving analyte, enzyme, and mediator (oxidized form) to correlate analyte concentration to diffusion limited current generated by oxidation of the reduced form of the mediator at the surface of the working electrode.)

After reaction is complete, a power source (e.g., a battery) applies a potential difference between electrical conductors 70, 71. When the potential difference is applied, the amount of oxidized form of the mediator at the counter electrode and the potential difference must be sufficient to cause diffusion-limited electro-oxidation of the reduced form of the mediator at the surface of the working electrode. Meter 12 measures the diffusion-limited current generated by the oxidation of the reduced form of the mediator at the surface of the working electrode. The measured current may be accurately correlated to the concentration of the analyte in sample when the following requirements are satisfied:

1. The rate of oxidation of the reduced form of the mediator is governed by the rate of diffusion of the reduced form of the mediator to the surface of the working electrode.
2. The current produced is limited by the oxidation of reduced form of the mediator at the surface of the working electrode.

Again, while an amperometric measurement is described, it is appreciated that current, charge, impedance, conductance, potential, or other electrochemically indicated property of sample may be accurately measured and correlated to the concentration of the analyte in sample with biosensor 10 and meter 12 in accordance with this disclosure.

Once the concentration of the analyte is determined, the user presses a button on meter 12 that activates motor 98 to rotate biosensor 10 in upper cavity 88 until a fresh capillary channel 20 lies adjacent to opening 124 in meter 12. Thus, biosensor 10 is set and in the proper position to undergo a subsequent test. Biosensor 10 is formed to rotate in meter 12 to conduct a pre-determined number of tests, which is based upon the number of capillary channels 20. Once each channel 20 in biosensor 10 has been exposed to opening 124, meter 12 alerts user that biosensor 10 is spent and should be replaced.

To manufacture biosensor 10, top and bottom sections 14, 18 are injection molded from a polycarbonate such as Novarex®. Next, the electrical conductors 71, 70 are applied to top and bottom sections 14, 18 with sputtering as will be readily understood by one of ordinary skill in the art. Reagent 72 is positioned on electrical conductor 70 over flanges 30. Additionally, spacer 16 is punched out of a film into the desired shape and positioned upon electrical conductor 70 spaced-apart from flanges 30. Top section 14 is situated on spacer 16 and apertures 52, 66, and 46 are situated in general alignment with one another. Top section 14, spacer 16, and bottom section 18 are then coupled together with connector pins 68.

Meter 12 is manufactured by injection molding shell 74, lid 82, partition 86 and door 110. Preferably, meter 12 is constructed of methylmethacrylate/acrylnitrile/butadine/styrene polymer (MABS) commercially available from BASF Aktiengesellschaft, Ludwigshafen, Germany. Plastics Drive system 94 is positioned in recessed portion 128 of shell 74 and partition 86 is snap-fit over a portion of system 94 so that drive wheel 100 is exposed in upper cavity 88 of meter 12. In addition, lid 82 is snap-fit onto walls 78 of shell 74 (FIG. 7) and door 110 is snap fit between tabs 150 of recessed portion 128. See FIG. 9A. Electronic components are situated in meter 12 beneath cover 80. It is appreciated that meter may be constructed in any number of manners as will be readily understood by one of ordinary skill in the art.

Figure 11:
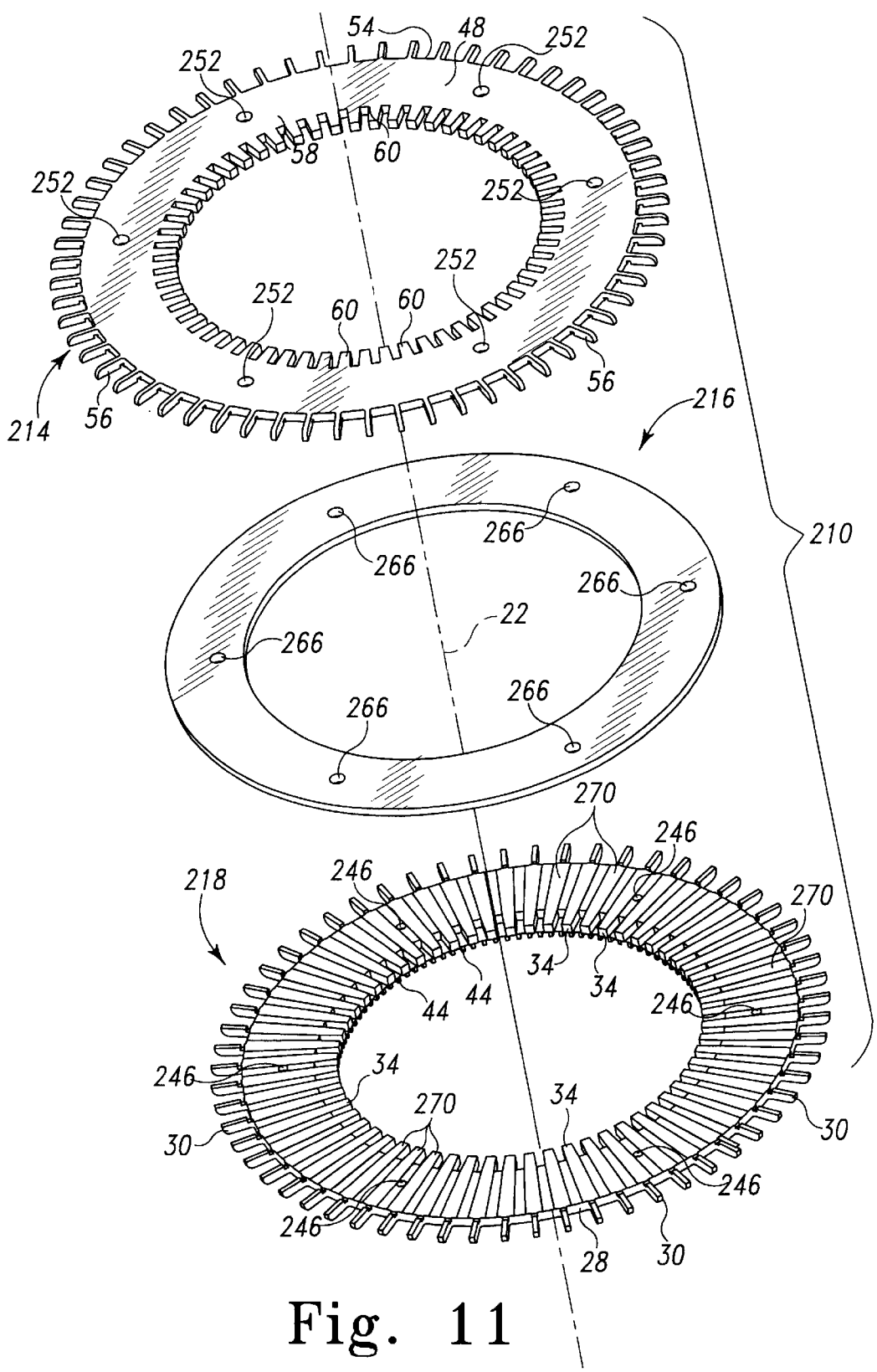
FIG. 11 is an exploded assembly view of a biosensor according to a further aspect of the invention.
Figure 12:
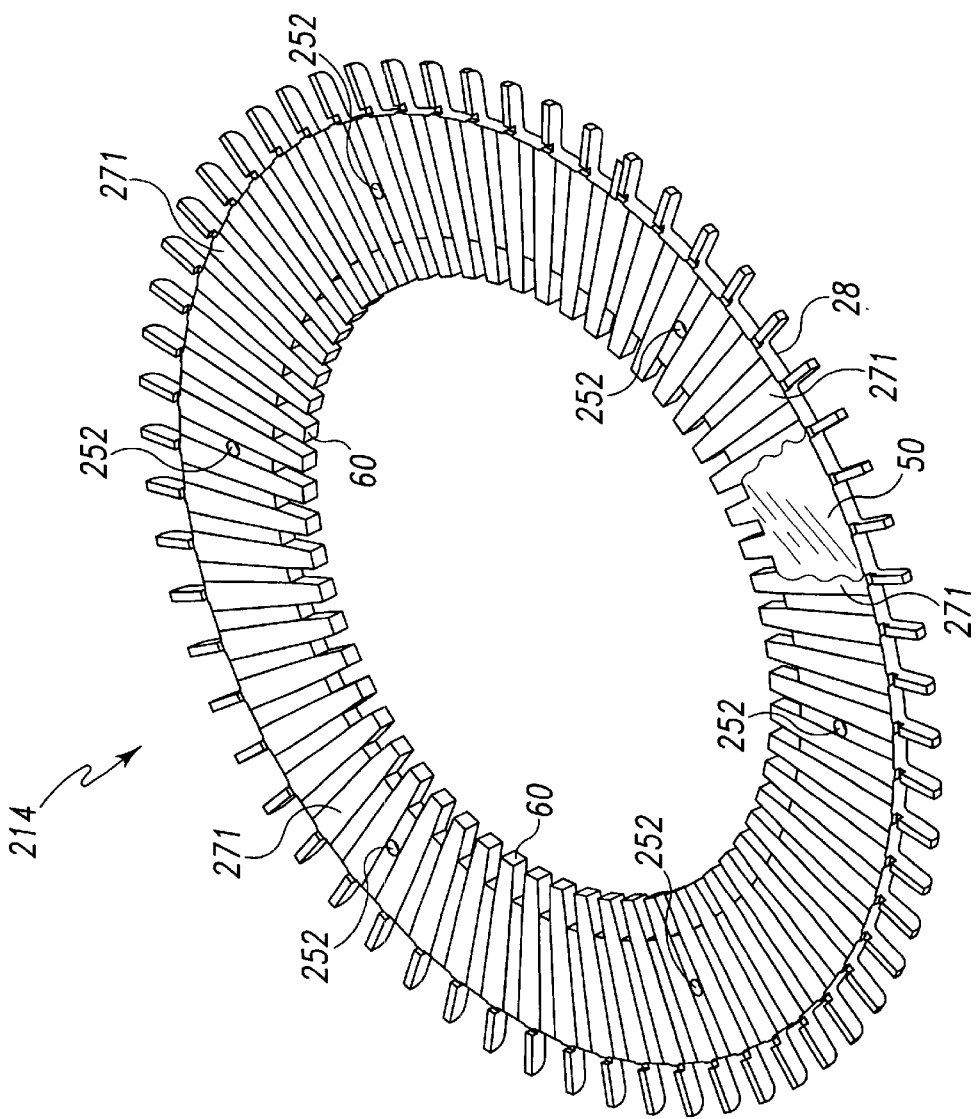
FIG. 12 is a bottom perspective view of the top ring section of the biosensor of FIG. 11 with portions broken away.

A biosensor 210 is provided in accordance with another aspect of this invention and is illustrated in FIGS. 11–12. Biosensor 210 includes top and bottom sections 214, 218 that are separated by a spacer 216. Top and bottom sections 214, 218 each include a series of spaced-apart tracks 270, 271. As shown in FIG. 11, each track 270 extends between one outer flange 30 and one inner flange 34 of bottom section 18. Likewise, as shown in FIG. 12, each track 271 extends between one outer flange 56 and one inner flange 60 of top section 14. In addition, bottom section 218 is formed to include six apertures 246 extending between elevated portion 40 of outer side 24 and inner side 26. Top section 214 also includes six apertures 252 that lie in general alignment with apertures 246 when biosensor 210 is assembled. Further, spacer 216 is formed similarly to spacer 16 except that it includes six apertures 266 that lie in alignment with apertures 246, 252. It is appreciated that top section 214, bottom section 218, and spacer 216 may include greater or fewer than six apertures in accordance with this disclosure.

Biosensor 210 is installed in meter 12 in a manner identical to biosensor 10 as previously described. In use, a liquid sample (not shown) is deposited between outer flanges 30, 56 into capillary channel 20. Capillary action draws the sample containing the analyte through channel 20 to dissolve reagent 72. The reaction between the analyte and the reagent occurs as that discussed above with reference to biosensor 10 and a power source applies a potential difference between tracks 270, 271. Meter 12 measures the diffusion-limited current across tracks 270, 271. The measured current may be accurately correlated to the concentration of the analyte in sample as previously described.

Biosensor 210 is constructed in a manner similar to biosensor 10, except that tracks 270, 271 are formed on sections 214, 216 by removing strips of the conductive material between tracks 270, 271, thus exposing inner sides 50, 26 of sections 214, 218. Removal of the conductive material is accomplished by machining the conductive material from sections 214, 218. Alternatively, it is appreciated that tracks 270, 271 may be formed by selective sputtering process as will be readily understood by one of ordinary skill in the art in accordance with this disclosure. Top section 214, spacer 216, and bottom section 218 are then coupled together with connector pins 68.

Figure 13:
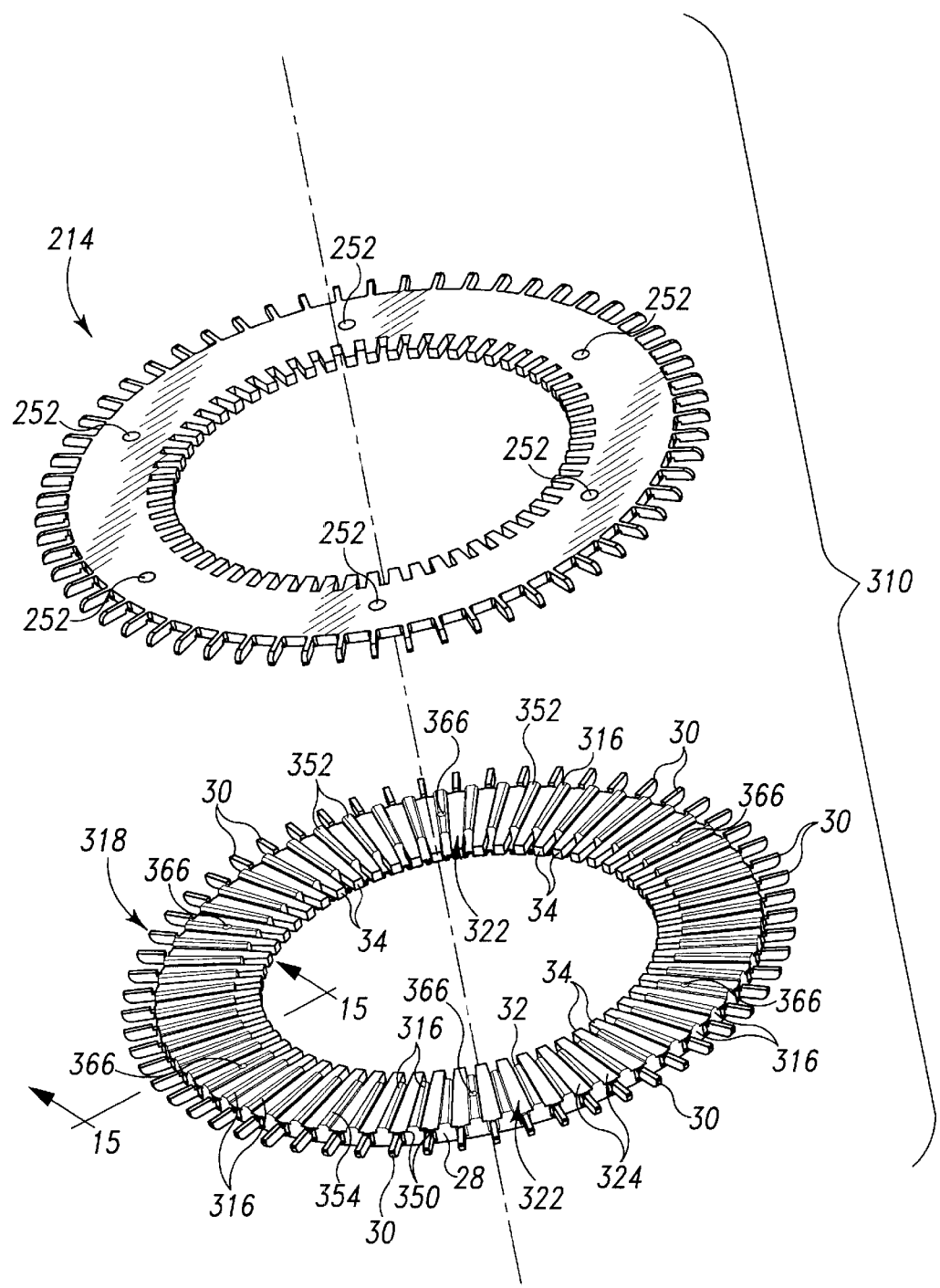
FIG. 13 is an exploded assembly view of a biosensor according to another aspect of the invention.
Figure 14:
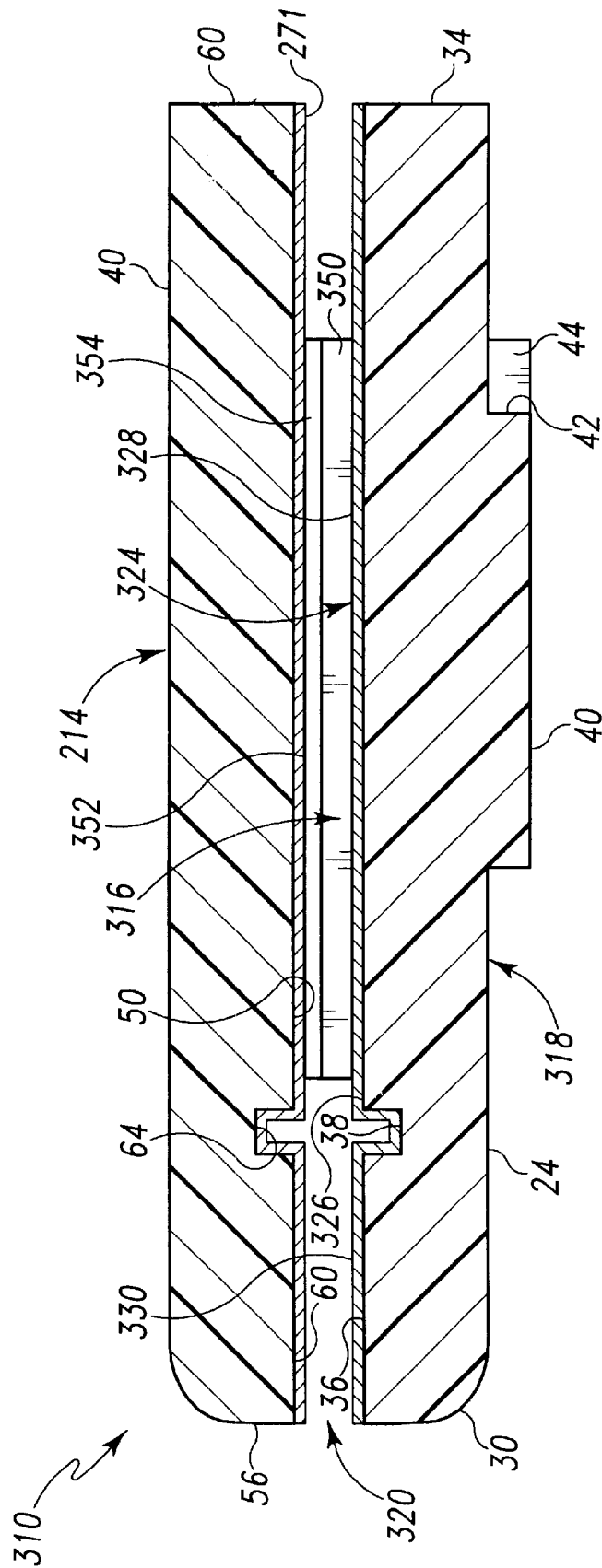
FIG. 14 is a cross-sectional view of the biosensor of FIG. 13 following assembly.

A biosensor 310 is provided in accordance with another aspect of this invention and is shown in FIGS. 13–14. Biosensor 310 is formed to cooperate with meter 12 in a manner identical to biosensors 10, 210. Biosensor 310 includes top ring section 214 and a bottom ring section 318. Top and bottom sections 214, 318 cooperate with one another to define a plurality of spaced-apart cantilevered capillary channels 320.

Referring now to FIG. 14, bottom section 318 of biosensor 310 includes an inner side 326 facing top section 214. Inner side 326 includes a plurality of supports 316 that are spaced-apart from one another and cooperate to define channels 322. Each support 316 extends between outer and inner edges 28, 32 and lies between aligned flanges 30, 34. Supports 316 include walls 350, a top side 352, and opposite beveled portions 354 extending between walls and top side 318, 320. Top section 314 is supported on top side 352 of supports 316 to position inner sides 50, 326 apart a distance sufficient to prevent electrochemical events at inner side 326 from causing an electrochemical event at inner side 50. It is appreciated that height of supports 316 may vary and that top and bottom sections 314, 318 may include greater or fewer than six apertures 252, 366 in accordance with this disclosure.

An electrical conductor 324 is laid down into each channel 322 and extends along walls 350 of each support 316. Conductor 324 serves as one electrode of biosensor 310, similar to electrical conductor 70 of biosensor 10. Conductor 324 includes a base 328 extending through channel 322 and a perimeter 330 at outer edge of flange 30 to place outer flange 30 and inner flange 34 of bottom section 318 in electrical communication with one another.

Biosensor 310 is installed in meter 12 in a manner identical to biosensor 10. In use, a liquid sample (not shown) is deposited between outer flanges 30, 56 into capillary channel 220. Capillary action draws the sample containing the analyte through channel 220 to dissolve reagent 72. The reaction between the analyte and the reagent occurs as that discussed above with reference to biosensor 10 and a power source applies a potential difference between electrical conductors 324, 271. Meter 12 measures the diffusion-limited current across conductors 324, 271. The measured current may be accurately correlated to the concentration of the analyte in sample as previously described.

Biosensor 310 is constructed in a manner similar to biosensor 10, except that plate 318 is molded in a manner to include supports 316. An electrical conductor is coated across the supports 316 and channels 322. The supports are then beveled as shown in FIG. 13, so that a gap exists between the electrical connector in channel 322 and the electrical connector on top surface 352 of support 316. Top section 214 is then positioned on top surface 352 of bottom section 318 so that apertures 252, 366 are in alignment. Top section 214 and bottom section 318 are then coupled together by connector pins 68 that extend through apertures 252, 366.

Although the invention has been described in detail with reference to a preferred embodiment, variations and modifications exist within the scope and spirit of the invention as described and defined in the following claims.

What is claimed is:

1. A biosensor comprising:
    a bottom section including an edge and a flange extending from the edge;
    a spacer positioned on the bottom section spaced-apart from the flange of the bottom section;
    a top section supported on the bottom section by the spacer, the top section including an edge and a flange extending from the edge of the top section in alignment with the flange of the bottom section, the flanges of the top and bottom sections cooperating to form a capillary channel;
    a first electrode positioned on the flange of the bottom section in the capillary channel; and
    a second electrode positioned on the flange of the top section in the capillary channel.

2. The biosensor of claim 1, further comprising a reagent positioned on at least one of the first and second electrodes.

3. The biosensor of claim 1, wherein the top and bottom sections are ring-shaped and have spaced-apart inner and outer edges.

4. The biosensor of claim 3, wherein each flange extends from the respective outer edges of the top and bottom sections.

5. The biosensor of claim 3, wherein the top and bottom sections each include a plurality of flanges extending from the respective outer edges.

6. The biosensor of claim 5, wherein the second electrode extends from the flange of the top section to the inner edge of the top section.

7. The biosensor of claim 3, wherein the first electrode extends from the flange of the bottom section to the inner edge of the bottom section.

8. The biosensor of claim 1, wherein the bottom section includes inner and outer edges and teeth adjacent to the inner edge.

9. The biosensor of claim 8, wherein the bottom section includes inner and outer surfaces and the teeth are positioned on the outer surface.

10. The biosensor of claim 1, wherein the top and bottom sections include a plurality of flanges.

11. The biosensor of claim 1, wherein the first electrode includes spaced-apart tracks.

12. The biosensor of claims 11, wherein the second electrode includes spaced-apart tracks.

13. A biosensor comprising:
    a bottom section including an edge and a flange extending from the edge;
    a top section supported on the bottom section, the top section including an edge and a flange extending from the edge of the top section in alignment with the flange of the bottom section, the flanges of the top and bottom sections cooperating to form a capillary channel;
    a first electrode positioned on the flange of the bottom section in the capillary channel; and
    a second electrode positioned on the flange of the top section in the capillary channel, wherein the top and bottom sections are ring-shaped and have spaced-apart inner and outer edges.

14. The biosensor of claim 13, wherein each flange extends from the respective outer edges of the top and bottom sections.

15. The biosensor of claim 13, wherein the top and bottom sections each include a plurality of flanges extending from the respective outer edges.

16. The biosensor of claim 15, wherein the second electrode extends from the flange of the top section to the inner edge of the top section.

17. The biosensor of claim 13, wherein the first electrode extends from the flange of the bottom section to the inner edge of the bottom section.

18. A biosensor comprising:
    a bottom section including an edge, a flange extending from the edge;
    a top section supported on the bottom section, the top section including an edge and a flange extending from the edge of the top section in alignment with the flange of the bottom section, the flanges of the top and bottom sections cooperating to form a capillary channel,
    a first electrode positioned on the flange of the bottom section in the capillary channel; and
    a second electrode positioned on the flange of the top section in the capillary channel, wherein the bottom section includes inner and outer edges and teeth adjacent to the inner edge.

19. The biosensor of claim 18, wherein the bottom section includes inner and outer surfaces and the teeth are positioned on the outer surface.

20. A biosensor comprising:
    a bottom section including an edge and a flange extending from the edge;
    a top section supported on the bottom section, the top section including an edge and a flange extending from the edge of the top section in alignment with the flange of the bottom section, the flanges of the top and bottom sections cooperating to form a capillary channel;
    a first electrode positioned on the flange of the bottom section in the capillary channel; and
    a second electrode positioned on the flange of the top section in the capillary channel, wherein the top and bottom sections include a plurality of flanges.

21. A biosensor comprising:
    a bottom section including an edge and a flange extending from the edge;

a top section supported on the bottom section, the top section including an edge and a flange extending from the edge of the top section in alignment with the flange of the bottom section, the flanges of the top and bottom sections cooperating to form a capillary channel;

a first electrode positioned on the flange of the bottom section in the capillary channel, the first electrode [includes] including spaced-apart tracks; and a second electrode positioned on the flange of the top section in the capillary channel.

22. The biosensor of claim 10, wherein the second electrode includes spaced-apart tracks.

23. A biosensor comprising:

a first electrode including a base and a perimeter extending about the base, a spacer situated on the base of the first electrode spaced-apart from the perimeter, and a second electrode including a base situated on the spacer and a perimeter, the perimeters of the first and second electrodes cooperating to define a cantilevered capillary channel.

24. The biosensor of claim 13, further comprising a reagent positioned between the first and second electrodes.

25. The biosensor of claim 23, wherein the bases of the first and second electrodes are each ring-shaped.

26. The biosensor of claim 23, wherein the base of the first electrode is formed to include spaced-apart tracks.

27. The biosensor of claim 26, wherein the base of the second electrode is formed to include spaced-apart tracks.

28. A biosensor comprising:

a first electrode including a base and a perimeter, a spacer situated on the base of the first electrode, a second electrode including a base situated on the spacer and a perimeter, the perimeters of the first and second electrodes cooperating to define a cantilevered capillary channel and the base of the first electrode is formed to include spaced-apart tracks.

29. The biosensor of claim 28, wherein the base of the second electrode is formed to include spaced-apart tracks.

30. A biosensor comprising:

a bottom section, a first electrode positioned on the bottom section and including a base and a perimeter extending about the base, a spacer positioned adjacent to the base of the first electrode, and a second electrode including a base positioned adjacent to the spacer and a perimeter, the perimeters of the first and second electrodes cooperating to define a capillary channel spaced-apart from the spacer.

31. The biosensor of claim 30, wherein the bases of the first and second electrodes each include spaced-apart tracks in alignment with one another.

32. The biosensor of claim 31, wherein the spacer is positioned to lie between the tracks of the first and second electrodes.

33. DOW A biosensor comprising:

a bottom section, a first electrode positioned on the bottom section and including a base and a perimeter, a spacer positioned adjacent to the base of the first electrode, and a second electrode including a base positioned adjacent to the spacer and a perimeter, the perimeters of the first and second electrodes cooperating to define a capillary channel, wherein the bases of the first and second electrodes each include spaced-apart tracks in alignment with one another.

34. The biosensor of claim 33, wherein the spacer is positioned to lie between the tracks of the first and second electrodes.

* * * * *